United States Patent [19]

Braun

[11] Patent Number: 5,662,928

[45] Date of Patent: Sep. 2, 1997

[54] METHOD FOR THE PREVENTION OR REMOVAL OF CRYSTALLINE SCOPOLAMINE IN A NON-AQUEOUS MATRIX OF A TRANSDERMAL SYSTEM

[75] Inventor: Richard L. Braun, Colts Neck, N.J.

[73] Assignee: Ciba-Geigy Corporation, Tarrytown, N.Y.

[21] Appl. No.: 426,166

[22] Filed: Apr. 21, 1995

[51] Int. Cl.$^6$ .......................... A61K 9/70; A61K 31/395; A61M 5/44

[52] U.S. Cl. ............................................. 424/449; 514/906

[58] Field of Search ............................. 424/448, 449; 604/307; 514/23; 546/129

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 4,031,894 | 6/1977 | Urquhart et al. | 128/268 |
| 4,201,211 | 5/1980 | Chandrasekaran et al. | 128/268 |
| 4,262,003 | 4/1981 | Urquhart et al. | 424/267 |
| 4,832,953 | 5/1989 | Campbell et al. | 424/468 |

*Primary Examiner*—Edward J. Webman
*Attorney, Agent, or Firm*—Marla J. Mathias

[57] ABSTRACT

A method for the prevention or removal of undesired crystals of scopolamine from a non-aqueous matrix of a transdermal system in which the scopolamine is dispersed is disclosed wherein the method comprises dynamically heating the scopolamine containing layer during the process of or immediately prior to assembling two laminates which once assembled encase the scopolamine containing layer.

20 Claims, No Drawings

METHOD FOR THE PREVENTION OR REMOVAL OF CRYSTALLINE SCOPOLAMINE IN A NON-AQUEOUS MATRIX OF A TRANSDERMAL SYSTEM

FIELD OF THE INVENTION

This invention relates to scopolamine transdermal drug delivery systems in which the scopolamine is dispersed in a polymer matrix. The invention further relates to the prevention or eradication of crystals of scopolamine in the matrix.

BACKGROUND

Dispersions of drugs and other substances in non-aqueous, typically polymeric, matrices are commonly used as reservoirs for various delivery devices. Representative devices are described in U.S. Pat. No. 3,598,122 (corresponding to Belgium 769155 and South Africa 7104095) and 3,598123 (corresponding to Belgium 769155) to Zaffaroni et at; U.S. Pat. Nos. 4,031,894 and 4,262,003 to Urquhart et at; and U.S. Pat. No. 4,201,211 (corresponding to GB 1577259, CH 646876, DE 2755661, and FR 239190) to Chandrasekaran et at; all of which are incorporated herein by reference. Transdermal devices for the administration of scopolamine of the type disclosed by Urquhart et al have been used extensively for the prevention of motion sickness. In U.S. Pat. No. 4,832,953 (corresponding to EP 304227), also incorporated herein by reference, Campbell et al report that transdermal scopolamine systems manufactured in accordance with the Urquhart reference above began to develop scopolamine hydrate crystals after 5 years of manufacturing systems without hydrate crystals appearing. The hydrate crystal problem worsened over the next two years to the point of significantly adversely affecting the release rate of scopolamine from the transdermal device.

These products were manufactured, according to Campbell et at, by solvent casting of chloroform solutions of scopolamine base in polyisobutene (PIB) and mineral oil (MO) onto impermeable webs to form drug reservoir and adhesive fills. Upon evaporation of the chloroform, a dispersion of liquid scopolamine base in the PIB/MO matrix forms. The drag reservoir and adhesive films there were then laminated to opposite sides of a release rate controlling membrane (the membrane formed from a mineral oil impregnated film). The resulting completed system had a removable release liner lamina, an adhesive lamina, a rate controlling membrane lamina, a drug reservoir lamina, and an impermeable backing lamina. Once the lamina were assembled, the systems were die cut and packaged in individual heat sealed foil pouches.

After another two years, the problem reported by Campbell et al became so severe that commercial production had to be halted until a solution was found. In an attempt to solve that problem, Campbell et al heat treated each of the reservoir laminate, the adhesive laminate and the multilaminate overnight with no visible effect. The casting solutions there were also heat treated and allowed to stand for extended periods with no effect. Since the problem found by Campbell et al was the formation of hydrate crystals, various attempts to remove water were tried, but again to no avail.

Against this background, Campbell et al found that if the assembled and cut (and preferably packaged) systems are heated to above the melting point of the scopolamine hydrate crystals, upon cooling to ambient temperature, the hydrate crystals did not reappear. Cambell et al reports heating the finished systems to a temperature of 60° C. (the scopolamine hydrate crystals melt at 59° C.) and holding the systems there for a period of 24 hours.

It has now been observed that systems which have been manufactured according to Campbell et al, have begun to develop an additional crystal which is not eliminated by the Campbell et al heating step. The crystals have been identified as being a higher melting (67°–70° C.) polymorph of hydrated scopolamine base. Attempts to solve this problem by merely raising the temperature at which the finished systems are heated in the Campbell process have been unsuccessful. While the crystals which form are melted, the result is a system wherein the distribution of active is vastly different from that in the original systems, thereby resulting in systems having vastly different release properties.

OBJECTS OF THE INVENTION

It is an object of the invention to provide a transdermal scopolamine system which is substantially free of scopolamine crystals.

It is another object of the invention to provide a method of avoiding scopolamine crystals in a scopolamine containing transdermal system.

It is another object of the invention to provide a method of eliminating scopolamine crystals from a scopolamine containing transdermal system.

SUMMARY OF THE INVENTION

These and other objects of the invention are achieved by heating the scopolamine containing lamina immediately before or during the process of laminating it to the rate control release membrane in addition to the heat treatment step set forth in Campbell et at.

DETAILED DESCRIPTION OF THE INVENTION

The present invention is a modification of the manufacturing process for a scopolamine transdermal deliver system which system comprises in sequence (1) a backing layer which is impermeable or substantially impermeable to scopolamine, (2) a scolpolamine reservoir layer which is itself made of a dispersion of scopolamine in a PIB/MO matrix, (3) a release rate controlling membrane layer, (4) an adhesive layer, and (5) a removable release liner. The release liner is removed just prior to applying the device to the skin of the user.

In the past, these devices were made by sovent casting a chloroform solution of scopolamine base in PIB and MO onto impermeable webs and the chloroform evaporated to create reservoir and adhesive films. The release rate control membranes were formed from MO impregnated microporous films. The reservoir film side of the impermeable web backed reservoir film was then laminated to one side of the control membrane and the adhesive side of the impermeable web backed adhesive film was laminated to the other side of the control membrane. These two laminations can be conducted without regard to order or can be conducted simultaneously. It is either immediately before or during these laminations of the scopolamine containing layers to the control membrane that the instant invention step takes place. Once the various impermeable web backed layers are laminated to the control membrane, the systems are die cut and subjected to the heat treatment step of Campbell et al to avoid the hydrate crystals reported there.

The present invention, which surprisingly eliminates the present higher melting point scopolamine hydrate crystals, is therefore the provision of an additional heating step just prior to or actually in the the process of laminating the scopolamine containing layers to the control membrane. Such crystals had not previously appeared and based on the experience seen in Campbell et al, and, especially the failure of simply raising the completed packaged dosage form heating step temperature, one would not have expected a heat treatment as in the present invention to work. After all, the heat treatment of the finished systems, which is still being carried out in accordance with Campbell et al is not sufficient to avoid the presently found crystals.

As stated above, the laminations can occur in any order, but the heating step should occur within about 24 hours, preferably within about 18 hours of the depositing of the scopolamine containing fire. In an ideal manufacturing setting, the film is deposited onto a web and the introduced into an oven to drive off the chloroform. The two webs are then brought together, while still in the oven and the annealing process of the invention takes place. In situations where the manufacturing equipment is not suited to a single oven (largely due to space limitations), each of the webs (the drug resevoir web and the contact adhesive web) have their respective solutions placed upon them and are introduced to a single or into two separate drying ovens. The dried webs emerge from the drying ovens and are brought together and introduced into an annealing oven. In other situations, where only one oven is available and which can only accomodate a single web at a time, the drug reservoir film is coated with scopolamine containing formulation and dried. The dried web is rolled and preferably rewound onto another roller while the contact adhesive is cast onto a web and dried. The contact adhesive may or may not have scopolamine in it, and preferably does have scopolamine. The dried contact adhesive web is rolled. Then the rolled dried contact adhesive and the rolled (preferably rerolled) drug reservoir containing film are brought in contact and introduced into the oven for the annealing process. This separate processing may also be needed when the throughput speeds of the various films differ.

Stock impermeable web backed reservoir and adhesive layers and stock control membranes are prepared as set forth above. In the case where the reservoir and the adhesive are separately laminated to the control membrane, each of the stock layers (reservoir/control membrane, and adhesive) are fed through heating chambers (preferably 35 feet long) over a period of 12–22 minutes, preferably about 15 to about 10 minutes, more preferably about 17.5 minutes for the reservoir layer and over a period of about 5–15 minutes, preferably about 7.5–12.5 minutes, more preferably about 10 minutes for the contact adhesive containing layer, before being brought together and annealed. The annealing operation can take place within the heating chamber or once the pre-annealed systems have emerged from the heating chamber. The annealing process takes place in a heating chamber (preferably about 35 feet) over a period of about 5–15 minutes, preferably about 7.5–12.5 minutes, more preferably about 10 minutes. The drying steps take place at about 60°–90° C., while the annealing step takes place at an oven temperature of from at least 67° to about 90° C., preferably at about 70° C. to about 90° C., more preferably about 80° C. to about 90° C., and most preferably at about 82° C.

In an alternative embodiment, the backing layer is coated with the scopolamine reservoir solution, dried to drive off the chloroform, laminated with the control membrane and annealed prior to being rolled on a roller.

In the case where the reservoir/control membrane and adhesive layer/release liner are formed laminated together, and annealed in a single process, the above conditions can be optimized to give the best results, but the oven traveling speeds of the webs must be adjusted so that the adhesive/release liner speed matches the reservoir/control membrane speed and the annealing speed. In the single assembly alternative here, the overall processing speed of the various webs is preferably 3.5 feet/minute through the various heating zones.

The invention will be more fully explained, but is not limited, by the following examples:

EXAMPLES

A chloroform solution containing mineral oil (MO), polyisobutylene (PIB), and scopolamine is coated, using an appropriate casting head, onto an ethylene/vinyl acetate (EVA) surface of a moving multi-layered polymer film (polyethylene, polyester, aluminum, EVA). The film is passed through an oven to remove the chloroform. The drug reservoir film exiting the oven is wound onto a core with a polyester interleaf. The roll of film of 1,250 ft is rewound and repassed through the oven at a temperature of 67°–90° C. at a speed of 2 feet/minute and again wound onto a core.

A similar chloroform solution containing scopolamine at a lower concentration is coated onto a moving polyester film and passed through an oven to remove chloroform. As the film exits the oven, a polypropylene film, saturated with MO, is pressure laminated to the contact adhesive film and a roll of 1,250 ft. of laminate is wound on a core with a polyester interleaf.

The drug reservoir film previously made is then pressure laminated to the contact adhesive film while removing the interleafing films. The final laminate is passed through an oven at a temperature range of 67°–90° C. at a speed of 3.5 ft per minute and wound onto a core.

The heat treated final laminate is die cut into individual systems, placed in pouches and placed in an oven at 75° C. for 24 hours.

We claim:

1. A process for the production of a scopolamine free base containing transdermal system substantially free of crystals of hydrated scopolamine free base, comprising annealing scopolamine free base containing layers of said transdermal system at a temperature of at least 67° C. for about 5 minutes-about15 minutes within about 24 hours of casting a scopolamine free base containing formulation onto a web for use in constructing said transdermal system.

2. The process of claim 1 wherein said transdermal system is further packaged and further heat treated at a temperature of at least 67° C. to about 90° C. for a period of about 12 to about 36 hours.

3. The process of claim 1 wherein said transdermal system is further packaged and further heat treated at a temperature of at least 67° C. to about 90° C. for a period of about 18 to about 30 hours.

4. The process of claim 1 wherein said transdermal system is further packaged and further heat treated at a temperature of at least 67° C. to about 90° C. for a period of about 22 to about 26 hours.

5. The process of claim 1 wherein said transdermal system is further packaged and further heat treated at a temperature of at least 70° C. to about 90° C. for a period of about 12 to about 36 hours.

6. The process of claim 1 wherein said transdermal system is further packaged and further heat treated at a temperature of about 82° C. for a period of about 12 to about 36 hours.

7. The process of claim 1 wherein said annealing takes place at about 67° C. to about 90° C.

8. The process of claim 1 wherein said annealing takes place at about 70° C. to about 90° C.

9. The process of claim 1 wherein said annealing takes place at about 82° C.

10. The process of claim 1 wherein said annealing takes place for a scopolamine containing reservoir layer over a period of about 10.5 minutes to about 22.5 minutes.

11. The process of claim 1 wherein said annealing takes place for a scopolamine containing reservoir layer over a period of about 17.5 minutes.

12. The process of claim 1 wherein said annealing takes place for a scopolamine containing contact adhesive layer over a period of about 5–15 minutes.

13. The process of claim 1 wherein said annealing takes place for a scopolamine containing contact adhesive layer over a period of about 10 minutes.

14. The process of claim 1 wherein a drug reservoir layer containing scopolamine free base and a contact adhesive layer containing scopolamine free base are each separately annealed and then contacted and sealed together.

15. The process of claim 1 wherein a drug reservoir layer containing scopolamine free base and a contact adhesive layer containing scopolamine free base are each separately annealed, then contacted and further annealed prior to packaging.

16. The process of claim 1 wherein a drug reservoir layer containing scopolamine free base is annealed, then contacted with a contact adhesive containing layer and then further annealed prior to packaging.

17. The process of claim 1 wherein a drug reservoir layer containing scopolamine free base is contacted with a contact adhesive layer and then annealed prior to packaging.

18. The process of claim 1 wherein a contact adhesive layer containing scopolamine free base is contacted with a layer drug reservoir layer and then annealed prior to packaging.

19. In a method for manufacturing delivery devices for the transdermal administration of scopolamine which comprises, in combination:

a. forming a laminate, at least one lamina of which comprises a dispersion of said scopolamine in a non-aqueous matrix;

b. cutting subunits forming said delivery devices from said laminate;

c. packaging said delivery devices in sealed containers;

d. heating said delivery devices in said containers to a temperature above the melting point of crystalline scopolamine hydrate and maintaining said delivery devices at such temperature for a time sufficient to prevent the formation or eliminate the presence of crystals of scopolamine hydate for a substantial period of time after cooling of the subunits to ambient temperatures; and e. cooling the delivery devices to ambient temperature;

the improvement comprising heating at least each scopolamine containing layer which also has one surface thereof exposed to the environment to a temperature of at least 67° C. up to 90° C. and maintaining this temperature for a period of about 5 minutes to about 22.5 minutes which improvement heating step is conducted prior to but within about 24 hours, or during the process, of laminating and/or sealing the scopolamine containing layer exposed surface.

20. The process of claim 19 wherein said step d is carried out at a temperature of at least 67° C. to about 90° C. for a period of about 12 to about 36 hours.

* * * * *